US007785346B2

(12) United States Patent
Blumberg

(10) Patent No.: US 7,785,346 B2
(45) Date of Patent: Aug. 31, 2010

(54) HEADACHE REDUCTION METHOD AND APPARATUS

(76) Inventor: Alan J. Blumberg, 950 Vernon Rd., Bexley, OH (US) 43209

( * ) Notice: Subject to any disclaimer, the term of this patent is extended or adjusted under 35 U.S.C. 154(b) by 1056 days.

(21) Appl. No.: 11/407,619

(22) Filed: Apr. 20, 2006

(65) Prior Publication Data

US 2006/0265023 A1 Nov. 23, 2006

Related U.S. Application Data

(60) Provisional application No. 60/682,778, filed on May 19, 2005.

(51) Int. Cl.
*A61B 17/00* (2006.01)

(52) U.S. Cl. ........................................................ 606/204

(58) Field of Classification Search .................. 606/204
See application file for complete search history.

(56) References Cited

U.S. PATENT DOCUMENTS 4,320,760 A * 3/1982 Sun et al. .................... 606/204
5,662,679 A * 9/1997 Voss et al. .................. 606/204
6,138,790 A * 10/2000 Leight ........................ 181/130
6,296,652 B1 * 10/2001 Qingmin ..................... 606/189
6,458,146 B1 * 10/2002 Kramer ...................... 606/204
2003/0059071 A1 * 3/2003 Dunham ..................... 381/309

* cited by examiner

*Primary Examiner*—Todd E. Manahan
*Assistant Examiner*—Jonathan A Hollm
(74) *Attorney, Agent, or Firm*—Steptoe & Johnson PLLC

(57) ABSTRACT

The invention relates to method and apparatus for relieving headaches. The method broadly comprises the step of applying a sufficient force to a given area of the triangular fossa region of the patient's ear for a sustained period of time effective for treating the patient by reducing the perceived pain of the headache. Apparatus is disclosed for employing the method, the apparatus comprising a banded earplug device having a biased headband positionable about the head of the patient and a pair of pods at opposite ends of the biased headband. The pods are placeable in compressive engagement with an area of the triangular fossa region in each of the patient's ears.

8 Claims, 2 Drawing Sheets

12
10
14
18
16
20
22
17
15

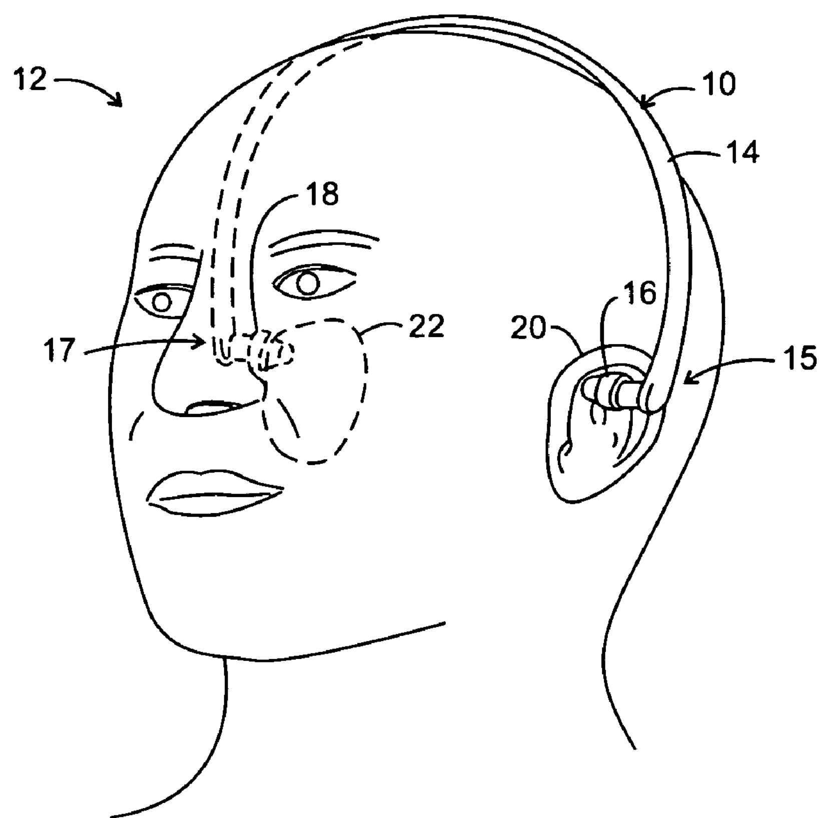
FIG. 1
FIG. 2
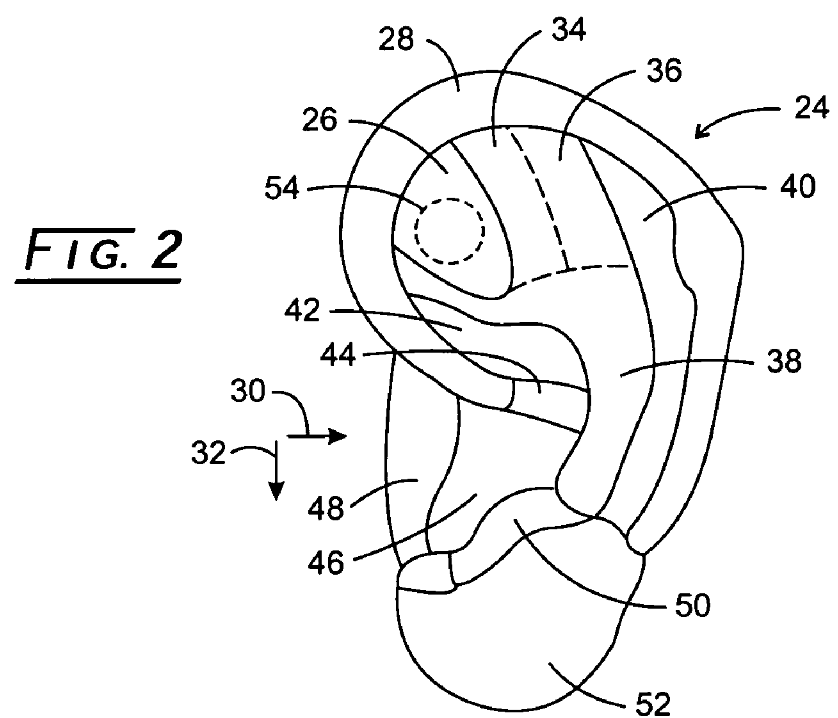

HEADACHE REDUCTION METHOD AND APPARATUS

CROSS-REFERENCE TO RELATED APPLICATIONS

This application claims the benefit of provisional Application No. 60/682,778, filed May 19, 2005, the disclosure of which is hereby incorporated by reference.

STATEMENT REGARDING FEDERALLY SPONSORED RESEARCH

Not applicable.

BACKGROUND OF THE INVENTION

The present invention relates generally to method and apparatus for reducing headaches, and especially migraine headaches. People have tried many techniques to relieve the pain of migraine headaches. Many of these techniques involve the application of pressure against blood vessels at the surface of the upper portion of the person's head, and especially at the temples (the flattened spaces at the opposite sides of the forehead). It often was thought that such pressure might reduce the blood supply to some portion of the head that was involved in the headache. The pressure was usually applied by the person who had the headache to him or herself, as with the thumbs, forefinger and/or middle finger of each hand. After applying pressure for perhaps a minute, the person's arm grew tired and he/she stopped.

Medicines have been developed that are effective in the reduction of the pain of migraine headache. The most popular medicine is IMITREX sold by GlaxoSmithKline, which currently has sales of about $1.2 billion per year. One of the problems with the use of this medicine is its cost to patients (without insurance), of $21 per 25 milligram pill (which gives relief in about one hour), $29 per 5 milligram nasal spray (which gives relief in about 20 minutes), and more than $100 for an injection in an emergency room (which gives relief in about 10 minutes). This medicine relieves headache symptoms by stimulating nerves in the head. The high cost for each treatment constitutes a burden for many people. As such, the art continues to seek improvements in relieving headaches.

BRIEF SUMMARY OF THE INVENTION

This invention provides method and apparatus for reducing headaches. The method comprises the application of a sufficient force to a given area of the triangular fossa region of a patient's ear for a sustained period of time effective for treating the patient by reducing the perceived pain of the headache. The apparatus of the invention may be used to employ the method and comprises a banded earplug device having a biased headband that may be positioned about the head of the patient and a pair of pods at opposite ends of the biased headband. When the headband is located on the patient's head, the pods may be placed in compressive engagement with an area of the triangular fossa region in each of the patient's ears.

BRIEF DESCRIPTION OF THE DRAWINGS

For a fuller understanding of the nature and advantages of the present invention, reference should be had to the following detailed description taken in connection with the accompanying drawings, in which:

FIG. 1 is a perspective view of a patient wearing the inventive headband;

FIG. 2 is a simplified perspective of a human ear showing a plurality of ear regions;

DETAILED DESCRIPTION OF THE INVENTION

Figure 3:
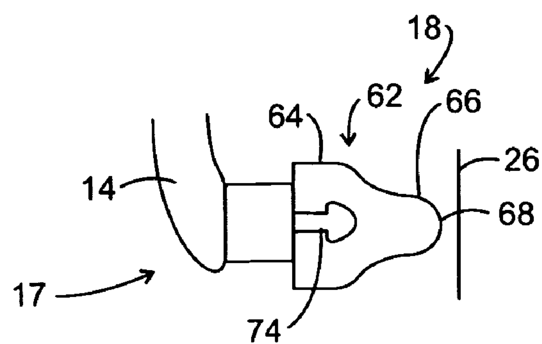
FIG. 3 is a perspective view of an earplug pod spaced apart from the triangular fossa region of the ear.

Applicant has found that a headache, or perceived pain in the head of the patient, and especially a migraine headache, can be successfully treated by applying pressure to particular areas of the person's ears for a sustained period of time. Applicant has found that the prolonged pressure may be readily applied to a patient's ears by a banded earplug device of the type described in U.S. Pat. No. 6,138,790 or of the type sold under the brand name QB2 HYG by Howard Leight Hearing Protection. FIG. 1 shows a banded earplug device, 10, positioned about the head, 12, of a patient. Banded earplug device 10 includes an injected molded band 14 extending between a left end, 15 and a right end, 17. Located at left end 15 and right end 17 are a pair of elastomeric plastic foam pods, 16 and 18. Pod 16 is connected to left end 15, while pod 18 is connected to right end 17. Pods 16 and 18 may be permanently connected to ends 15 and 17. Alternatively, pods 16 and 18 may be releasably connected to ends 15 and 17. For example, after one or more uses, pods 16 and 18 may be disposed of and new pods reconnected to ends 15 and 17. Pods 16 and 18 are placed against the patient's left and right ears, 20 and 22, respectively. Band 14 applies a force to the head of about one-half to about three-quarters pound when worn on the head. Such banded earplug devices are used in large numbers to protect workers' hearing in factories, with the pods entering the ear canal of the workers to block noise. These earplugs are available at a cost of a few dollars each, which is far below the expected cost for a new medical device, especially a reusable one, and which can be even less than a single dose of available medication for a migraine headache. Also, the instrument does not require a prescription and does not have possible side effects of medicine.

Rather than being positioned in the patient's ear canals, banded earplug device 10 has been modified so that each of the pods 16 and 18 is placed in compressive abutting adjacency with the triangular fossa region of the ear. As shown in FIG. 2, the human outer ear, 24, has been mapped by dividing it into several regions, usually based on the topography (small "hills, valleys, ridges and recesses") of the outer ear. One area of particular interest is the above-noted "triangular fossa" region, seen at 26, lying immediately (within about 2 cm.) rearward and downward of the helix, 28. The rearward direction is illustrated by directional arrow 30, while the downward direction is illustrated by directional arrow, 32. Adjacent triangular fossa region 26 is the upper antihelix region, which includes a front portion 34 and a back portion 36. Downward of the upper antihelix region is the antihelix region, 38. Rearward of antihelix region 38 is the scaphold fossa region, 40. Successively downward of the antihelix region 38 are the superior concha, 42, the concha ridge, 44, and the inferior concha, 46. Inferior concha 46 also is rearward of the tragus region, 48. Downward from inferior concha 46 is the antitragus, 50. Located at the bottom of ear 24 is lobe 52.

Applicant finds that one may treat the perceived pain caused by a headache by applying a sufficient force to a given area, 54, of triangular fossa region 26 for a sustained period of time. For example, when a force of about 11 ounces is applied continually, for a period of at least about 3 minutes, and preferably at least 6 minutes, to area 54 of about 0.5 square centimeter in the triangular fossa region 26, the symptoms of a headache and especially a migraine headache are often significantly relieved.

Applicant uses banded earplug device, or instrument, 10 of the type described above in connection with FIG. 1 by spreading pods 16 and 18 apart and placing them against the triangular fossa region 54 of each ear, instead of within the inferior concha, or ear canal, 46. Device 10 then is allowed to remain in place without being hand held, with the biasing of the band causing pods 16 and 18 to continue to press against the triangular fossa region 26. After a sufficient length of time, e.g., about 6 to 8 minutes, headache symptoms are greatly relieved and the device can be removed. Alternatively, device 10 may be left on indefinitely.

Figure 4:
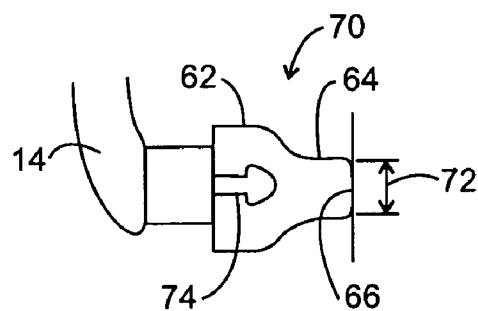
FIG. 4 is a perspective view of the earplug pod abutting the triangular fossa region of the ear.

FIGS. 3 and 4 show elastomeric pod 16 of FIG. 1 in greater detail as it is placed next to and in abutting engagement with ear 22. Elastomeric pod 18 has the same configuration as pod 16. Each foam pod has an initial shape such as shown at 62 in FIG. 3, including an outer portion, 64, and a tapered inner portion, 66, extending to an inner end, 68. Inner portion 66 generally is tapered at an angle of less than about 45°. In FIG. 3, pod 18 is positioned with inner end 68 spaced slightly apart from triangular fossa region 26 of ear 22. In FIG. 4, inner end 68 of pod 18 has been placed in compressive abutting adjacency with triangluar fossa region 26 such that pod 18 has the compressed shape indicated generally at 70. In this figure, it may be seen that inner portion 66 flattens against triangular fossa region 26 and the flattened pod end 68 applies a force of between about 4 ounces to about 24 ounces over an area of a diameter, 72, of about 0.8 centimeters, to apply the force of about 11 ounces over an area of about 0.5 $cm^2$. This area of applied force is indicated at 54 in FIG. 2.

FIGS. 3 and 4 also show an insert 74 of the much stiffer plastic of band 14 projecting into the pod. This minimizes the possibility that the pod will bend over instead of compressing.

A migraine headache is an often familial symptom complex of periodic attacks of vascular headache, usually temporal and unilateral in onset, commonly associated with irritability, nausea, vomiting, constipation or diarrhea, and often photophobia. Applicant's study of literature concerning migraine headaches shows that they are caused by increased blood flow resulting from vasodilation of cranial blood vessels. Specifically, in the area inward of the triangular fossa region, there is a triangular fossa-associated nerve bundle that includes the great auricular nerve, the lesser occipital nerve, the auricular-temporal branch of the trigeminal nerve and the vagus nerve (which is associated with nausea and dizziness). Migraine attacks are preceded by constriction of the cranial arteries and commence with the vasodilation (vascular dilation) that follows. This vasodilation creates increased blood flow which is believed to irritate the underlying triangular fossa-associated nerve bundle, and, in particular, the auricular-temporal branch of the trigeminal nerve. Applicant's application of pressure to the triangular fossa region results in the application of pressure to the dilated blood vessels. When the banded earplug instrument is removed, or even left on after a plurality of minutes, the wearer often achieves headache relief. This relief is believed to be due to the now-constricted blood vessel ceasing to irritate the auricular-temporal branch of the trigeminal nerve.

Some people may have their triangular fossa-associated nerve bundle (which includes the auricular-temporal branch of the trigeminal nerve bundle) at the rear of the triangular fossa or even in the front portion 34 of the upper antihelix shown in FIG. 2. Such people may find relief by placing the instrument pods in the area 34 or at the border of the triangular fossa region, 26 and front portion 34.

Figure 5:
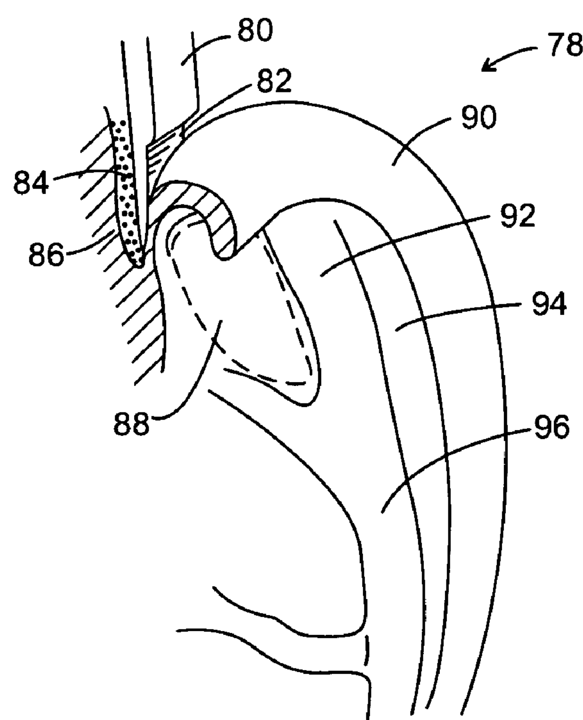
FIG. 5 is a perspective view of an earplug pod abutting an alternative area directly inward of the top of the triangular fossa region.

As an alternative to using a band that presses against the triangular fossa of the ear, as shown in FIG. 2, it also is possible to use an instrument that presses elsewhere, but still adjacent the triangular fossa-associated nerve bundle or more specifically adjacent the auricular-temporal branch of the trigeminal nerve. FIG. 5 shows a biased one side of a hand-band, 80, that tapers to an end, 82. Attached to the inner side of end 82 is a small pod, 84. Tapered end 82 fits behind the patient's ear, 78, such that pod 84 presses directly against the head at a location, 86, directly inwardly of the top of the triangular fossa region, 88. As noted in FIG. 2, triangular fossa region 88 lies downwardly of helix, 90, with the upper antihelix, 92, and scaphold fossa regions, 94, being located rearwardly of triangular fossa region 88. Located downwardly of the triangular fossa region 88 is the anti helix region, 96.

Thus, the invention provides a low cost and simple instrument and method for relieving the symptoms of a headache, and especially a migraine headache. The method comprises the application of force against the triangular fossa of each ear of the patient, and possibly the front half of the upper antihelix. The force may be applied by an instrument in the form of a banded earplug which previously has been used to seal the ear canal to block sound. The instrument includes a biased headband which has elastomeric pods at its opposite ends that press with a force, e.g., on the order of magnitude of 4 to 24 ounces, against opposite ears of the wearer's head. The instrument is installed and left in place against the triangular fossa of each ear for a period of a plurality of minutes, for example, at least 3 minutes and often at least 6 minutes, to reduce headache symptoms.

A study by Applicant shows that the symptoms of a headache are greatly reduced by the procedure. Since the symptoms of pain of a headache are not yet measurable by instruments, the efficacy of the banded earplug device currently can only be determined by statements of the patient. In Applicant's study, three patients were enrolled. At the time of enrollment, each patient indicated that she was presently experiencing a headache. Each patient was subject to a physical assessment including the following information: age and gender of the patient; whether any symptoms existed before the headache onset; whether the patient had ever been diagnosed with migraine headaches; the medications currently being taken, including both over the counter and prescription medications; the onset time of the headache being experienced; and the patient's head circumference.

Following recordation of the physical assessment, each patient was asked to evaluate the headache pain perceived using the Wong-Baker FACES Pain Rating Scale. The scale consists of six faces arranged in a horizontal format and ranging from happy to sad. A patient selects the particular face represents the level of his or her perceived pain. Since each face is associated with a given pain rating, the tester can determine the degree or extent of the patient's perceived pain. Specifically, at the far left of the scale, a smiley face indicates a pain rating of zero (0) or "No Hurt". The next face to the right, which has a slightly less exaggerated smile, indicates a pain rating of two (2) or "Hurts Little Bit". Moving down the scale, the next face, which is neither smiling nor frowning, indicates a pain rating of four (4) or "Hurts Little More". The next face is slightly frowning and indicates a pain rating of six (6) or "Hurts Even More". Continuing down the row, the next face is a more exaggerated frown and indicates a pain rating of eight (8) or "Hurts Whole Lot". The last face in the series is a crying and frowning face that indicates a pain level of ten (10) or "Hurts Worst".

After evaluating the patient's perceived pain, the banded earplug device was applied to the patient with the pods positioned against the triangular fossa region of the patient's ears. Proper placement was confirmed and then a timer started. After six minutes elapsed, the patient's perceived pain was evaluated again using the Wong-Baker FACES Pain Rating Scale. After ten minutes, the banded earplug device was removed and the patient's perceived pain was evaluated again using the Wong-Baker FACES Pain Rating Scale. Two hours after removing the banded earplug device, the patient's perceived pain was evaluated using the Wong-Baker FACES Pain Rating Scale. After the conclusion of the test, patient's were asked for feedback regarding the efficacy of the banded earplug device. Each patient was assigned an identification number, and the test data for each patient was associated with the proper identification number.

TABLE I

| ID No. | Gender | Age | Pre-diagnosed (Yes or No) | Time Onset of Current Headache | Circumference | TF Vertical | TF Horizontal |
|---|---|---|---|---|---|---|---|
| 5367 | Female | 61 | No | Past 15 Days | 5.4 | 10 | 10 |
| 12150 | Female | 28 | Yes | 5:30 a.m. | 5.7 | 14 | 9 |
| 4291 | Female | 53 | Yes | 10:30 a.m. | 5.3 | 12 | 8 |

TABLE II

| ID No. | Initial Pain Evaluation | 6 minute Pain Evaluation | 10 Minute Pain Evaluation | 2 Hour Pain Evaluation |
|---|---|---|---|---|
| 5367 | 6 | 4 | 4 | 4 |
| 12150 | 8 | 2 | 2 | 2 |
| 4291 | 2 | 2 | 2 | NA |

From Table II, it may be seen that the procedure was effective in relieving the perceived headache pain in 2 out of the 3 patient's tested. In particular, it should be noted that the patient identified by number 12150 indicated in her patient history that she has been diagnosed with migraine headaches. In her initial evaluation, she indicated a perceived pain rate of 8. After wearing the banded earplug device for 6 minutes, her perceived pain rate dropped significantly from 8 down to 2. The patient continued to report a lowered pain rating of 2 even after the banded ear plug device had been removed for 2 hours. The patient identified by number 5367 also experienced a decrease in the perceived pain associated with her headache. In the initial evaluation, this patient indicated a perceived pain rate of 6. After wearing the banded earplug device for 6 minutes, she reported a lowered perceived pain rating of 4. This lowered rating again was reported 2 hours after removing the banded earplug device. The third patient reported neither an increase nor a decrease in perceived pain after wearing the banded earplug device.

While the invention has been described with reference to various embodiments, those skilled in the art will understand that various changes may be made and equivalents may be substituted for elements thereof without departing from the scope and essence of the invention. In addition, many modifications may be made to adapt a particular situation or material to the teachings of the invention without departing from the essential scope thereof. Therefore, it is intended that the invention not be limited to the particular embodiments disclosed, but that the invention will include all embodiments falling within the scope of the appended claims. In this application all units are in the metric system and all amounts and percentages are by weight, unless otherwise expressly indicated. Also, all citations referred herein are expressly incorporated herein by reference.

I claim:

1. A method for treating the perceived pain caused by a headache in a patient having an ear with a triangular fossa region, comprising the steps of:

(a) providing a banded earplug device having a pair of pods at opposite ends of a biased headband;

(b) positioning said headband about the head of said patient; and (c) placing said pods in compressive abutting adjacency with said triangular fossa regions of said patient's ears to apply a sufficient force to a given area of only said triangular fossa region for a sustained period of time effective for treating said patient by reducing said perceived pain.

2. The method of claim 1 wherein said force is applied adjacent the triangular fossa-associated nerve bundle comprising the auricular-temporal branch of the trigeminal nerve.

3. The method of claim 2 wherein said force is applied adjacent said auricular-temporal branch of the trigeminal nerve.

4. A method for reducing a headache in a patient, comprising the steps of:

(a) providing a handed earplug device having a pair of pods at opposite ends of a biased headband;

(b) positioning said headband about the head of said patient;

(c) placing said pods in compressive abutting adjacency with said triangular fossa regions of said patient's ears; and (d) applying a force at about 4 ounces to about 24 ounces for a sustained period of at least about 3 minutes only said triangular fossa regions of said patient's ear.

5. The method of claim 4, wherein said step (a) comprises applying said force at about 11 ounces.

6. The method of claim 4, wherein said step (a) comprises applying said force for a sustained period of about 6 minutes.

7. The method of claim 4, wherein said step (a) comprises applying said force to a 0.5 square centimeter area of said triangular fossa region.

8. The method of claim 4, wherein said pods are formed of elastomeric material.

* * * * *